(12) United States Patent
Hubis

(10) Patent No.: US 7,424,529 B2
(45) Date of Patent: Sep. 9, 2008

(54) SYSTEM USING HOST BUS ADAPTER CONNECTION TABLES AND SERVER TABLES TO GENERATE CONNECTION TOPOLOGY OF SERVERS AND CONTROLLERS

(75) Inventor: Walter A. Hubis, Louisville, CO (US)

(73) Assignee: International Business Machines Corporation, Armonk, NY (US)

( * ) Notice: Subject to any disclaimer, the term of this patent is extended or adjusted under 35 U.S.C. 154(b) by 654 days.

(21) Appl. No.: 10/832,800

(22) Filed: Apr. 26, 2004

(65) Prior Publication Data

US 2005/0050191 A1    Mar. 3, 2005

(51) Int. Cl.
*G06F 15/173* (2006.01)
(52) U.S. Cl. .................. 709/224; 709/223; 709/220; 709/249
(58) Field of Classification Search .......... 709/223, 709/224, 229, 246, 220, 249; 711/148, 5; 713/100; 714/37, 6, 5; 710/15, 17, 18, 19
See application file for complete search history.

(56) References Cited

U.S. PATENT DOCUMENTS

| | | | |
|---|---|---|---|
| 5,901,280 A | 5/1999 | Mizuno et al. | |
| 6,173,374 B1 * | 1/2001 | Heil et al. | 711/148 |
| 6,209,023 B1 | 3/2001 | Dimitroff et al. | |
| 6,295,575 B1 * | 9/2001 | Blumenau et al. | 711/5 |
| 6,343,324 B1 | 1/2002 | Hubis et al. | |
| 6,367,033 B1 | 4/2002 | Jibbe | |
| 6,381,642 B1 | 4/2002 | O'Donnell et al. | |
| 6,449,709 B1 | 9/2002 | Gates | |
| 6,457,139 B1 | 9/2002 | D'Errico et al. | |
| 6,480,901 B1 | 11/2002 | Weber et al. | |
| 6,480,955 B1 | 11/2002 | DeKoenig et al. | |
| 6,944,654 B1 * | 9/2005 | Murphy et al. | 709/223 |

* cited by examiner

*Primary Examiner*—Le Luu
(74) *Attorney, Agent, or Firm*—Kunzler & McKenzie

(57) ABSTRACT

Structure, system, apparatus, method, and computer program for managing and configuring a computer storage system by mapping the topology and connectivity of all servers, storage devices, and storage device controllers within the storage subsystem, based on unique identifiers especially WWN identifiers. The method includes querying a server to identify host bus adapters coupled to the server, querying each host bus adapter to identify attached device controllers, issuing a read connection information command to the device controller and returning the connection results including identifying devices coupled to the device controller, and storing the returned connection results in a data structure.

19 Claims, 6 Drawing Sheets

SYSTEM USING HOST BUS ADAPTER CONNECTION TABLES AND SERVER TABLES TO GENERATE CONNECTION TOPOLOGY OF SERVERS AND CONTROLLERS

RELATED APPLICATIONS

This application claims the benefit of priority to U.S. patent application Ser. No. 09/466,993 entitled Storage Network and Method for Storage Network Device Mapping, filed 10 Dec. 1999, and U.S. patent application Ser. No. 09/394,220 entitled System and Method for Host Volume Mapping for Shared Storage Volumes In a Multi-Host Computing Environment filed 13 Sep. 1999, which applications are hereby incorporated by reference.

FIELD OF THE INVENTION

This invention pertains generally to structure and method for managing and configuring a complex computer server and storage system, and more particularly to structure and method for managing and configuring array controllers in a storage subsystem by mapping the topology and connectivity of all servers, storage devices, and storage device controllers, based on unique identifiers.

BACKGROUND

Heretofore, management and configuration of storage device controllers, such as Redundant Array of Independent Disk (RAID) storage sub-system controllers, for complex server systems has been a difficult and frequently operator intensive task. For example, in the exemplary server system 102 configuration of FIG. 1, a client computer 104 is attached to a wide area network 106 or to a local area network 108, which is also attached to a variety of server systems 110, each attached to storage devices 112. In the system of FIG. 1, four servers (first server 110-1, second server 110-2, third server 110-3, and fourth server 110-4) are specifically illustrated; however, it should be clear that an arbitrary number of servers 110 may be provided, for example, N servers may be provided and configured into the system 102 along with any attached storage devices or storage subsystems 112. Server 110-1 is coupled to storage array 112-1 via a first array controller 116-1 over fibre-channel arbitrated loop (FC-AL) 120-1, server 110-2 is coupled to a plurality of storage devices 112-2 over a second fibre-channel arbitrated loop 120-2, and third server 110-3 and fourth server 110-4 are coupled to storage area network (SAN) including third storage subsystem 112-3 and fourth storage subsystem 112-4 controlled respectively by second array controller 116-2 and third array controller 116-3 as well as storage area network 118.

It is noted that server three 110-3 is attached to a storage area network 118, and has another server (server 110-4) attached in addition to storage devices 112-3, 112-4. In this example, all of the storage devices are attached via a Fibre Channel Arbitrated Loop (FC-AL), although other connection structures, protocols, and methods may be used, including for example parallel SCSI.

Client computer 104 is used to run the client software program 122 for performing and managing the configuration information for some and desirably all of the array controllers 116 in this exemplary system 102. This client software program 122 is typically stored in a memory and executed in a processor or CPU of the client computer, where execution allows a disk array or other storage subsystem (such as one of disk arrays 112-1, 112-2, 112-3, or 112-4) to be identified, selected, and managed.

Management functions may include for example, the configuration of storage attached to the array, and special protocol or hardware parameters, fibre channel settings and or addresses, and communication of exceptional events such as for example, disk failure, environmental problems, or the like) back to the client computer 104. A human operator 124 (identified but not part of the system) must program the client software 122 with specific information about the path from each array controller 116 to each server 110. In conventional systems, this mapping is currently accomplished by using either the SCSI ID or addresses 128 or the fibre channel ID or address 130 of each storage device, or by the device's World Wide Number (WWN) 132 which is unique for each fibre channel device manufactured. This is the address of the array controller 116, not the disks attached to the array 112. The array controller organizes the disks and presents them to the servers 110 under a different address. SCSI addresses 128, fibre channel addresses 130, and World Wide Number (WWN) 132 are known in the art, and not described in greater detail here.

Unfortunately, although conventional structures and methods for configuring and managing the system 102 and its components arguably provide acceptable performance, such conventional structures and methods using manual procedures, SCSI addresses or IDs 128, fibre channel addresses or IDs 130, and World Wide Number (WWN) 132 in the manner described, have problems and sever limitations. Finally, a WWN consists of 16 characters and it is frequently difficult or time consuming to determine the WWN of a disk or array controller simply by visual inspection, depending on the labeling of the storage device. The storage devices may be installed in a larger geographically diverse subsystem, making visual identification impossible.

For example, when SCSI IDs 128 or fibre channel IDs 130 are used, the SCSI ID or Fibre Channel ID of a device (such as of the disk array controllers 116 or disk drives 112-2) can change whenever the system configuration is changed. Any time a device is added or removed from a fibre channel arbitrated loop 120, all fibre channel loop addresses are renegotiated by the fibre channel loop initiators (for example, the servers 110), which may result in a device having a new ID, different from its ID prior to negotiation.

In any event, with any of the afore described addressing or identification schemes, the human operator 124 typically must manually collect the data before the computer can proceed. This can be a daunting task, especially when the storage network is large, or geographically distributed locations.

Therefore there remains a need for a method that overcomes these problems and limitations. In one aspect, the invention eliminates the need for visual inspection of the storage devices. It also eliminates the cumbersome and error prone approach of manually collecting and entering numbers for device addresses. Thus, the invention collects data and other information about the storage systems more quickly and with less errors than is possible using conventional manual approaches.

BRIEF DESCRIPTION OF THE DRAWINGS

For a better understanding of the nature and objects of the invention, reference should be made to the following detailed description taken in conjunction with the accompanying drawings, in which.

SUMMARY

Figure 1:
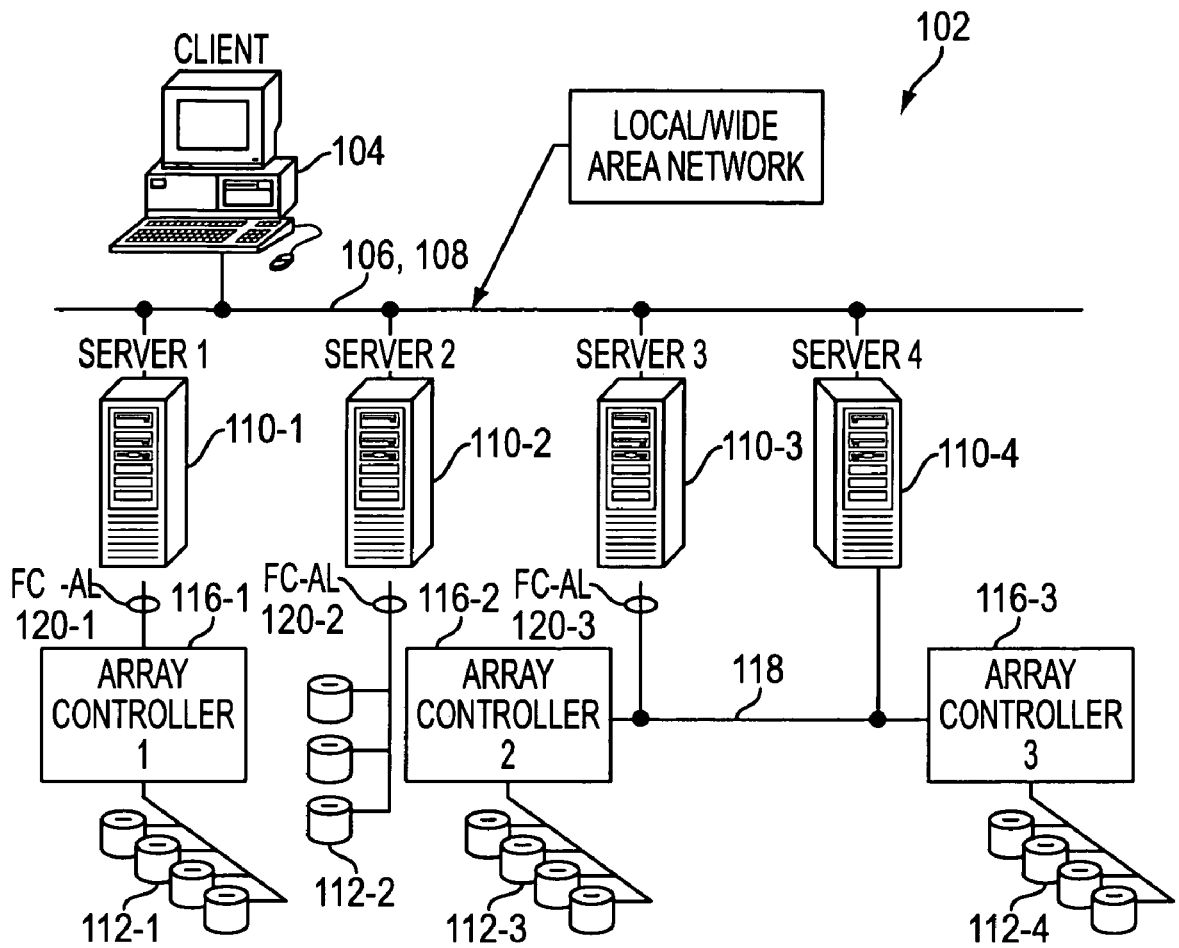
FIG. 1 is a diagrammatic illustration showing an exemplary storage system.

The invention provides structure, system, apparatus, method, and computer program for managing and configuring a computer storage system. Embodiments of the invention are particularly well suited for managing and configuring array controllers in a storage subsystem by mapping the topology and connectivity of all servers, storage devices, and storage device controllers within the storage subsystem, based on unique identifiers especially WWN identifiers.

In one aspect, the invention provides a method for collecting connection information for a computer system having a server, at least one device controller coupled to the server by a first communication channel, and a client coupled in communication with the server. The method includes: querying the server to identify all host bus adapters coupled thereto, querying each host bus adapter to identify all device controllers attached on the communication channel, issuing a read connection information command to the device controller and returning the connection results determined by the command including identifying all devices coupled to the device controller, and storing the returned connection results in a data structure. In one particular embodiment, the connection results include a server identifier, a host bus adapter identifier corresponding to the server, and at least one device controller identifier corresponding to a device controller coupled to the host bus adapter, and the data structure comprises a server identification table and at least one host bus adapter connection table associated with a particular host bus adapter. Each server identification table desirably stores at least one server identifier, and each host bus adapter is linked to at least one server table by a pointer and stores at least one device controller identifier. The host bus adapter identifier advantageously comprises a first WWN and the device controller identifier comprises a second WWN.

In another aspect, the invention provides a read connection information command for collecting connecting information for components coupled to a server, the components selected from the group consisting of bus adapters, device controllers, and devices coupled to the device controllers. In one embodiment, the read connection information command includes a direct command operation code field identifying the command to be executed, and an allocation length field indicating the number of bytes the initiator has allocated for information returned in connection with execution of the command. The command may also optionally include a Logical Unit Number field. In one embodiment, the command returns connection information selected from the group comprising an identifier of the Initiator issuing the command, an identifier of the controller receiving the command, an identifier of the partner controller, and other information. Some information may be optional. In one particular embodiment, the identifier of the Initiator issuing the command comprises a WWN of the Initiator issuing the command, the identifier of the controller receiving the command comprises a WWN of the controller receiving the command, and the identifier of the partner controller comprises a WWN of the partner controller.

In another aspect, the invention provides a storage subsystem controller including a processor, a memory coupled to the processor storing procedures and data, the data including a host interface connection table storing a host interface identifier and at least one storage system controller identifier, the procedures including a configuration client procedure, a host interface input/output processor; and a storage device interface input/output processor.

In other aspects, the invention includes a computer program in the form of computer software and/or computer firmware implementing the inventive procedures and method, a computer program product storing the inventive computer program in tangible form, a device controller utilizing the structure and method of the invention, and a computer system incorporating the inventive mapping method.

DETAILED DESCRIPTION OF EMBODIMENTS OF THE INVENTION

The invention will now be described in detail by way of illustrations and examples for purposes of clarity and understanding. It will be readily apparent to those of ordinary skill in the art in light of the teachings of this invention that certain changes and modifications may be made thereto without departing from the spirit or scope of the appended claims. Section headings, where provided in the detailed description, are for convenience and are not be construed as limiting the disclosure, as various aspects of the invention are described throughout the detailed description.

A structure, system, method, and computer program product for mapping and collecting information about storage in storage subsystems in a storage network, such as in a storage area network (SAN), including for example, a RAID system in a SAN, is described. Conventional operating systems and data exchange methods provide only limited information gathering facilities for multiple storage subsystems connected to multiple server systems. These conventional systems and methods prevent effective and simple management of the storage subsystems in homogeneous storage networks and makes management of heterogeneous networks, that is networks having more than one type of computers and/or differing operating system (i.e., Windows, Unix., Irix, Linux, and the like.) extremely difficult and in practical terms, nearly impossible. The inventive structure and method provides a messaging protocol that allows a storage configuration tool to identify all of the storage subsystems on a storage area network independent of the operating system or data channel type. In one embodiment, this method uses the World Wide Name (WWN) that is assigned to each Fibre Channel device to uniquely identify and locate that device. This structure and method is also applicable to complex configurations of storage area networks, servers, and wide area networks (WAN) for management and fault isolation.

The inventive structure, system, method, and computer program product allows a complex connection of server(s) and storage system(s) to be mapped for the purpose of managing and configuring storage device controllers, such as RAID array controllers.

Figure 2:
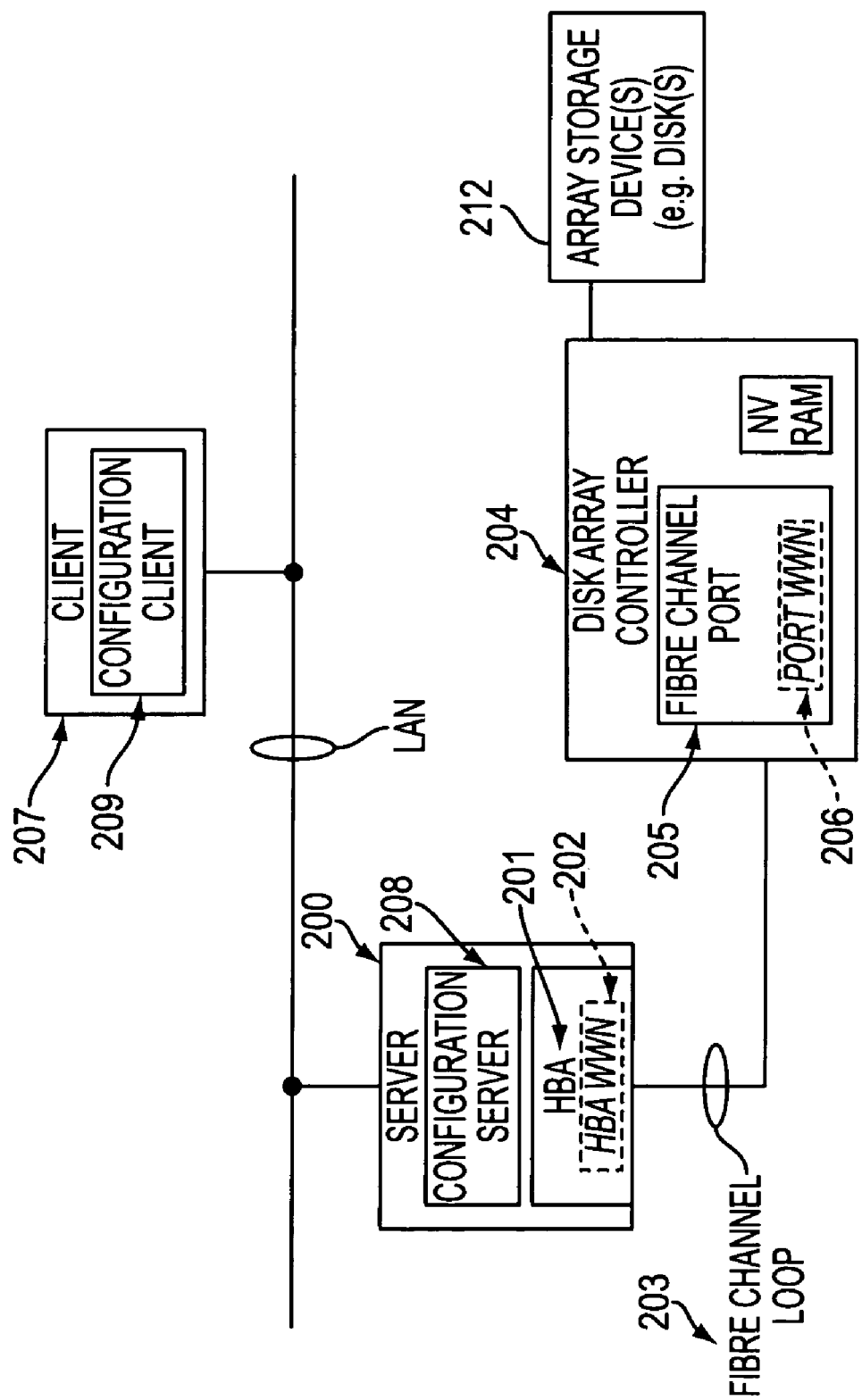
FIG. 2 is a diagrammatic illustration showing typical connections between a client, a server, and disk array controller.

With reference to FIG. 2 which illustrates one embodiment of the invention, the structure and method of the present invention provides and utilizes a novel SCSI direct command (referred to here as the Read Fibre Connection Information command) that allows the array storage device 212 to return the Port WWN 206 of the array controller 204. However, the invention is not restricted to SCSI commands and may be practiced with non-SCSI commands without departing from the invention. In addition, the HBA WWN 202 of the fibre channel host bus adapter (HBA) 201 to which the array storage device 212 is connected can be returned to the client computer 207 by the server 200. This allows the disk array controller 204 and the server HBA 201 to be uniquely identified by the client computer 207 and permits the connection between the array controller 204 and the server 200 to be identified by the client computer 207.

Configuration client 209 comprises an client application computer program 314 executing on the client computer 207. Configuration server 208 is an analogous computer program executing on the server computer 302. The structure and operation of the configuration client 209 and configuration client application program 314 as well as the structure and operation of the configuration server 208 and configuration server application program 313 are described in greater detail elsewhere in this description.

Figure 3:
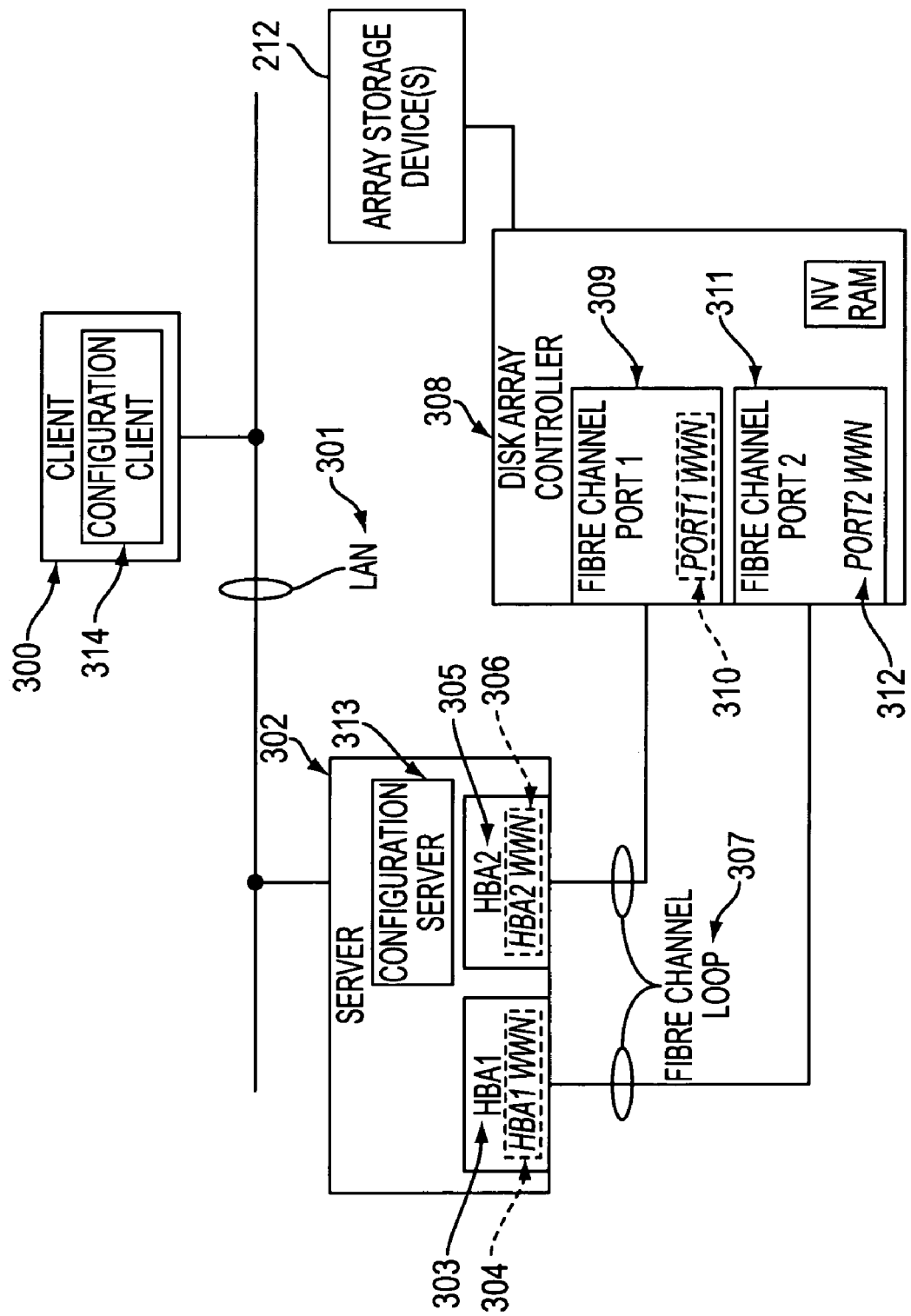
FIG. 3 is a diagrammatic illustration showing typical connections between a client, a server, and disk array controller, where the server includes a plurality of host bus adapters and the disk array controller includes a plurality of Fibre channel ports coupled to the host bus adapters.

FIG. 3 illustrates an embodiment of the invention wherein server 304 has a plurality of HBA's (HBA1 303 and HBA2 305) and a disk array controller 308 has a plurality of Fibre Channel Ports (Fibre Channel Port 1 309 and Fiber Channel Port 2 311). Each of these HBA and Fibre Channel Ports has a WWN.

Server 302 having more than one or multiple HBAs attached to the same array controller 308 provides fault tolerance through redundancy. The inventive structure and method also supports configurations in which clustered servers share a common data pool, such as the storage area network (SAN) shared by servers three 110-3 and four 110-4 in the system 102 of FIG. 1.

Each server 110, 200, 302 runs a local server counterpart of a configuration client 314 software program 313 known as the configuration server 313. This configuration server 313 software program allows specific configuration and control commands to be sent by the server computer 302 to the storage array (e.g. RAID disk array) controller 308 from the configuration client 314. The configuration client 314 software issues a command to the configuration server 313 software by way of the LAN 301. The configuration server 313 software configures a SCSI command that is issued to the array controller 308 by way of the fibre channel loop 307. The disk array controller 308 receives the command, executes the appropriate firmware, and returns the data to the configuration server 313 software by way of the fibre bus 307. The configuration server 313 software then returns this information to the configuration client 314 software by way of the LAN 301. In this way, the configuration server 313 software can be seen as an agent for the configuration client 314 software that is resident on the server computer 302. This is necessary, since the configuration client 314 software cannot communicate directly with the array controller 308, but must transfer data through the server computer 302. The configuration server 313 also allows information from the disk array controller 308 to be sent to the configuration client 314. The configuration client 314 software is made aware of which servers 110, 302 are connected to an array storage device (e.g. a RAID device) 212 through the operator's input. Each server computer 302 can be identified by an Internet Protocol (IP) address or by a host name that is a part of the protocol associated with the LAN 301. The IP address and hostname are interchangeable for the sake of this discussion. The operator inputs either the hostname or the IP address to the configuration client 314 software. This uniquely identifies the server commuters 302 that the configuration client 314 software will attempt to communicate with over the LAN 301. The operator specifies the servers 110 to which the client should connect by specifying the node name of the server 110, or the IP address of the server. The node name and IP address are standard Ethernet protocol conventions which are well known. Once this information is collected by the configuration client 314 software, the client software will begin to collect detailed connection information from the named server computers 302 by requesting that the configuration server 313 software issues the special Read Fibre Connection Information command, described in greater detail hereinafter, to any disk array controllers 308 connected to the server computers 302. While the phrase "Fibre Connection" is used to refer to a preferred embodiment of the command which is used in conjunction with a Fibre Channel based communication link, the inventive structure and method are not limited to such Fibre Channel based systems, and the command may more generally be referred to as a Read Connection Information command.

The inventive Read Connection Information (RCI) or Read Fibre Connection Information (RFCI) type command 550 is advantageously a vendor-unique command, although such a command may be incorporated into a standard protocol if desired. A vendor unique command is generally a command that allows the unique characteristics of the array controller (for example, those characteristics not defined in the SCSI or Fibre channel specifications and therefore possibly not available via standard SCSI or Fibre Channel commands or protocols) to be determined and set, as well as allowing other special operations to the disk array controller 308. As a result, issuing this RFCI command to any device other than a RAID controller will usually result in a SCSI Check Condition status for that command, and returning SCSI Sense Data with the Sense Key set to Illegal Command. These conditions are known in the art and are not described here in greater detail, except as necessary to describe special handling of the command as it relates to the invention. Thus, this method is beneficial only when used in conjunction with devices that support this RFCI type of command. The characteristics required by a device to support the Read Fibre Connection Information command are described below.

When a Read Fibre Connection Information command is issued to the array controller 308 via the Fibre Channel Arbitrated Loop (FCAL) bus 301, the array controller 308 will return the WWN of the array controller 310 and the WWN of the server HBA 306 to which the array controller 308 is connected or to a particular HBA of the server and Fibre Channel Port when the server and/or controller has multiple HBA's and/or ports. The data is returned in the SCSI Data Out phase of the SCSI command. The SCSI Data Out phase of the Read Fibre Connection Information command is defined within the SCSI specification, and allows transfers of data from the array controller 308 to the server HBA 303, 305. The SCSI protocol runs on top of the Fibre channel layer, so conformity to the SCSI protocol is required when the particular SCSI Read Fibre Connection Information command is used. The SCSI protocol is known in the art, and is not described here in greater detail except as needed to describe the invention. Other embodiments of the invention not relying on SCSI protocols need not conform to SCSI protocol.

For a controller to support the Read Fibre Connection Information command, that controller should support Fiber Channel connectivity and protocol, and have a processor and storage capacity that permits the inventive Read Fibre Connection Information command to be programmed or otherwise executed, and for the information returned to be stored and used. Some exemplary controllers that may be adapted to support the inventive Read Fibre Connection Information command are the Models DACFF, DACSF, or DACFFx series of RAID controllers made by Mylex Corporation of Fremont Calif. and Bolder, Colo.

One exemplary embodiment of the Read Fibre Connection Information command is now described relative to Table I, which identifies the elements of one particular embodiment of the command. The Read Fibre Connection Information command is sent to the array controller 308 using a Vendor Unique Command operation code (20h) in the controller firmware.

TABLE I

Exemplary Read Fibre Connection Information Command CDB Format.

| Byte/Bit | 7 | 6 | 5 | 4 | 3 | 2 | 1 | 0 |
|---|---|---|---|---|---|---|---|---|
| 0 | | | | Operation Code (20h) | | | | |
| 1 | | LUN | | | | Reserved | | |
| 2 | | | | DCMD OP CODE - OP_READ_FIBRE_CONNECTION_INFO (D4h) | | | | |
| 3 | | | | Reserved | | | | |
| 4 | | | | Reserved | | | | |
| 5 | | | | Reserved | | | | |
| 6 | | | | Reserved | | | | |
| 7 | | | | Allocation Length (MSB) | | | | |
| 8 | | | | Allocation Length (LSB) | | | | |
| 9 | | | | Control Byte | | | | |

In this exemplary Command Data Block (CDB) format, the LUN field contains the Logical Unit Number (LUN), which is optional and in most instances may be ignored since the Read Fibre Information command is not specific to a LUN. In some other SCSI command instances the LUN is desirably retained because it contains information necessary for the successful completion of a SCSI command. In the case of commands that are not specific to a LUN, or where the LUN is meaningless, the SCSI command specification allows the LUN field to be ignored. The Direct Command Opcode (CMD OP CODE) is the command to be executed, in this case the Read Fibre Connection Information command as identified in the "OP_READ_FIBRE_CONNECTION_INFO, D4h" fields of the CDB. The Allocation Length Field, both the Most Significant Byte (MSB) and the Least Significant Byte (LSB) indicate the number of bytes the initiator has allocated for information returned in the SCSI Data In phase of the command. If the length is zero, no data is transferred and this is not treated as a error condition. The controller 308 terminates the Data In phase when it has completed transfer of the requested number of bytes or all returned Read Fibre Connection Information data, whichever is less. All reserved fields and the Control Byte (which is ignored because the operation of this field does not affect the operation of the Read Fibre Information command) should be zero.

The Read Fibre Information command is issued by the configuration server 313 software to the disk array controller 308 through the server HBA 303, 305. Each HBA has a WWN 304, 306 that may or may not be known to the configuration server 313 software. In the general case, it is assumed that the configuration server 313 does not have access to the WWN 304, 306 of the HBA 303, 305. It is necessary for the configuration client 314 software to have knowledge of the WWNs 304, 306 in order to accurately determine the configuration of the SAN. This is especially true in the case where multiple servers are connected to multiple array controllers as illustrated in FIG. 1.

When the HBA 304, 306 begins communication with the disk array controller 308, it logs in to the disk array controller 308 through the array controller's Fibre Channel Port 309, 311. This process is defined in the Fibre Channel Arbitrated Loop specification. As a part of the Log In process, the HBA 303, 305 provides its WWN 304, 306 to the disk array controller. The array controller 308 retains this information. Since the array controller 308 already knows its own WWN 310, 312, all of the information required to return the HBA WWN 306 and the disk array controller WWN 310 is known by the disk array controller. The information is then returned to the configuration server 313 software as a part of the data returned by the disk array controller in response to the Read Fibre Information command.

The data returned to the initiator in response to the Read Fibre Connection Information command is described in Table II. Bytes 0-7 of the returned data are the WWN of the initiator issuing the RFCI command, or in the case of the FIG. 3 embodiment having multiple HBA's and/or controller ports, the WWN 306 of the particular HBA (for example HBA 305) of the server 302 issuing the command. Bytes 8-15 of the returned data are the WWN 310 of the Fibre Channel Port 309 of the array controller 308 receiving the Read Fibre Connection Information command. Bytes 16-23 are the WWN 312 of the second or partner Fibre Channel Port 311 of the array controller 308 receiving the command. If the array controller 204 does not have a second or partner fibre channel port such as in the embodiment illustrated in FIG. 2, this field is set to zero. Typically a controller 308 has two or dual ports. Certain types of controller hardware have only one Fibre Channel Port, while others have two, or some other plurality of Fibre Channel or other ports.

TABLE II

Description of data returned for the Read Fibre Connection Information command.

| Byte | Description |
|---|---|
| 0–7 | WWN of the Initiator issuing the command. |
| 8–15 | WWN of the controller receiving the command. |
| 16–23 | WWN of the partner controller. |

Attention is now turned to a description of an embodiment of the inventive method and procedures. A data transaction is an interaction between an initiator (in this case, for example, a server computer 302) and a Target (in this case, for example, an array controller 308). In this transaction, the initiator 302 has data to be written to the array controller 308, or read from the controller 308. The initiator sends a request to read or write data to the target in a format defined by the SCSI or other protocol. The target responds by returning the data the initiator requested (in the case of a read transaction), or by writing the data the initiator sent to the storage device via the target (in the case of a write transaction). At the start of any transaction, or set of transactions, the initiator logs in to the target. This login procedure or transaction is a conventional part of the Fibre Channel Arbitrated Loop (FC-AL) protocol, such as described in "Fibre Channel Arbitrated Loop Protocol (FC-AL2) X3.272 T11 Project 1133D Rev. 6.2", hereby incorporated by reference, and not described in greater detail here.

As a part of the login transaction, the target (in this case, array controller 308) is notified that an initiator (in this case, a server 302) is attempting to establish a connection with the array controller 308 through the server's HBA 305 and fiber channel loop 307. The WWN 306 of the server's HBA 305 is transferred to the array controller 308 through the array controller's fibre channel port 1 309. When this transaction has been completed, the array controller has both the WWN 306 of the HBA 305 attaching to the array controller and hence to the storage array, as well as the array controller's own WWN 310. The array controller's own WWN is encoded into a memory of the array controller, preferably a Non-Volatile Random Access Memory (NVRAM) of the array controller. Having the WWNs of the both the array controller and the server is useful in Storage Area Networks (SANs) and Host-to-Volume mapping were access to an array controller 308 is allowed or disallowed by the array depending on the WWN of the server. This applies to the case of servers 110-3 and 110-4 of FIG. 1, where access to an array controller 116 is to be limited to specific servers. Embodiments of host-to-volume mapping systems and methods are described in co-pending U.S. patent application Ser. No. 09/394,220 entitled System and Method for Host Volume Mapping for Shared Storage Volumes In a Multi-Host Computing Environment, which is hereby incorporated by reference.

The functionality provided by the Read Fibre Connection Information command, along with the configuration server software 313, server HBA WWN 306, and the disk array controller port WWN 310, permit the configuration client software 314 to locate all array storage devices and storage subsystems, and further map and determine the topology of any servers 110, 302 to which such storage devices and storage subsystems are attached. Where devices other than storage devices are attached to the system by other types of controllers, such devices and controllers may be mapped in analogous manner so that the invention is not limited to storage systems and storage array controllers but is broadly applicable to a variety of systems, controllers, and devices.

Typically, any particular client 104, 300 will have a specific set of servers 110, 302 to configure and/or manage, which are entered or otherwise identified by the administrator of the system. In some instances one client will be responsible for managing all the servers and their associated storage devices. The configuration client software 314 can then request that each server 302 query the attached array controller(s) 308 using the Read Fibre Connection Information command. Information regarding the WWN of each server HBA 305, 306 (HBA 1 WWN or HBA 2 WWN) and array controller WWN 309, 311 (Port 1 WWN or Port 2 WWN) is returned to the configuration client software 314 by the server 302 by using the configuration server software 313 resident on the server 302. The configuration client software 314 then generates a connection topology, such as in the form of a data structure identifying the topology and connectivity of array controllers 116, 308 that are attached to single and or multiple servers 110, 302. This topology information may be presented to the user in a variety of forms, including graphical representations, tabular representations, lists, or the like, and can be stored for future reference, analysis, and/or display.

Figure 4:
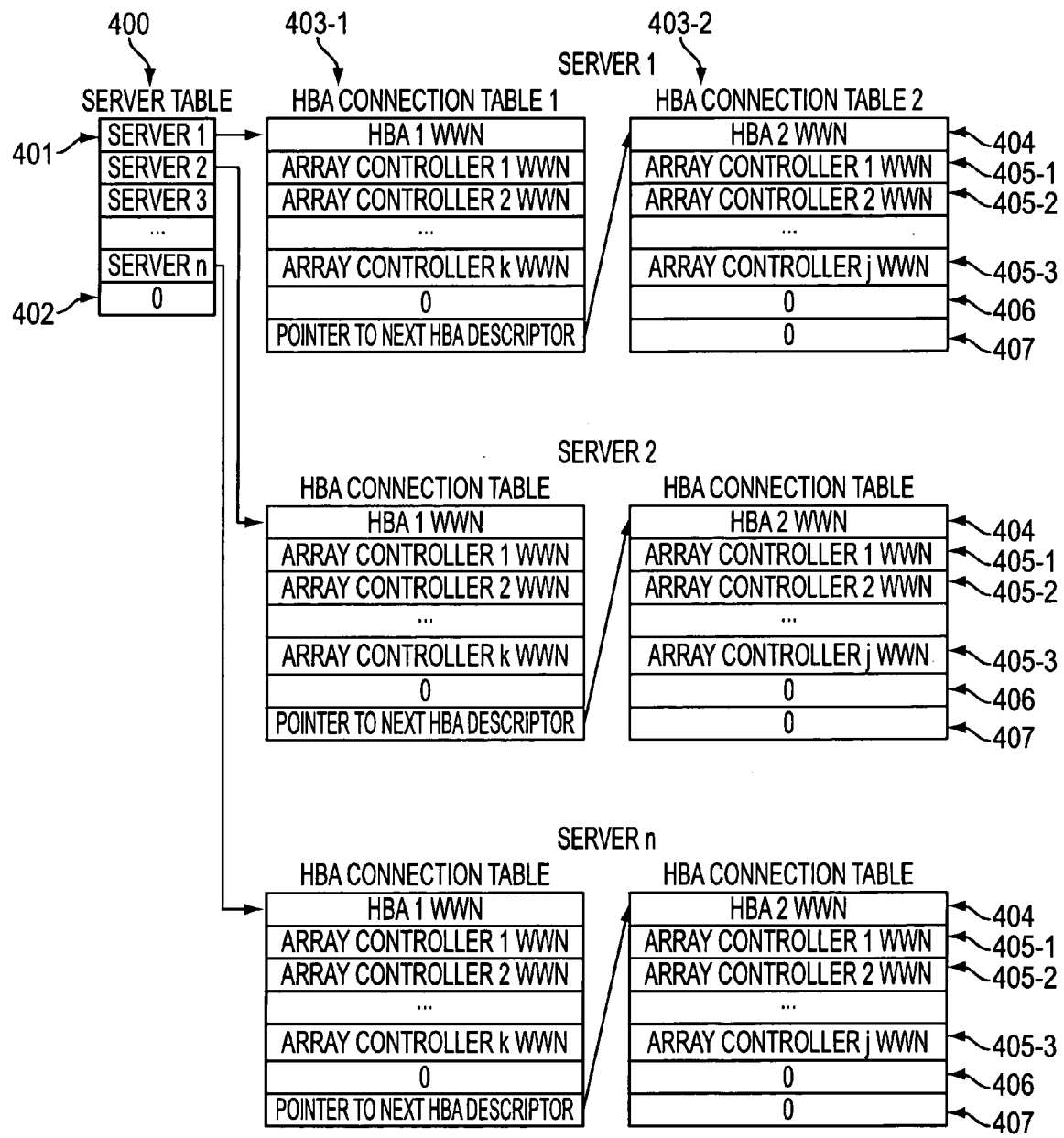
FIG. 4 is a diagrammatic illustration showing a exemplary data structures for a server table and for host bus adapter connection tables.

One embodiment of the data structure is now described relative to FIG. 4. Each server 302 (such as Server 1, Server 2, . . . , Server n) has or is associated with an entry 401 in the Server Table 400 (or list). These entries (401-1, 401-2, . . . , 401-n) each point to a particular HBA Connection Table (or list) 403, the HBA connection table being different for each entry 401. The server table 400 is maintained by the Configuration Client Software 314, and has one entry for each server 302 that is connected to least one array controller 308. The last entry in the Server Table 402 is set to zero to denote the end or last entry of the table.

The HBA connection tables 403 contain the WWN of each HBA 303, 305 connected to the server 302 and the WWN of each disk array controller 308 connected to the HBA. There is one instantiation of an HBA connection table 403 for each HBA 305 present on each server 302. Each set HBA connection tables 403 stores or contains the WWN of the server HBA 306 in the first position 404 of the table. Subsequent entries of the HBA connection tables 403 contain a list of WWNs 405 for each disk array controller 308 attached to that HBA, such as those attached to the HBA via the FC-AL loop 307. The next to last entry 406 in the HBA connection tables 403 always contains zero or some other predetermined indicator to indicate the end of the list of arrays attached to the HBA. The final entry 407 in the HBA connection table either points to the next HBA connection table 407 for that server 302 where such next HBA connection table exists, or is zero or some other indicator to denote that there are no further HBAs 305 attached to that server 302.

This method of mapping automatically collects information that is normally difficult or impractical to collect manually. Furthermore this information can be used to rapidly pinpoint faults in large storage systems by comparing storage maps from time to time to detect devices that are no longer attached to the SAN, devices that have been recently added to the SAN, or other anomalous conditions.

In one embodiment, the invention provides a method for collecting connection information for a computer system having a server, at least one device controller coupled to the server by a first communication channel, and a client coupled in communication with the server. The device controller may for example be a RAID or other storage system array controller controlling a device such as a storage subsystem, RAID array, or other controllable device or system. The method includes querying the server to identify all host bus adapters coupled thereto, querying each host bus adapter to identify all device controllers attached on the communication channel, issuing a read connection information command to the device controller and returning the connection results determined by the command including identifying all devices coupled to the device controller, and storing the returned connection results in a data structure. Where the computer system includes a plurality of servers and or a plurality of host bus adapters configured with or connected to the one or more servers, the inventive procedure is advantageously performed for all servers and all host bus adapters that are capable of interoperating with the inventive structure and method. In at least one embodiment of the inventive method, the information collection is initiated by a configuration client in conjunction with a configuration server and involves a read information command. In one embodiment, this read information command is adapted for Fibre Channel arbitrated loop communication links.

Figure 5:
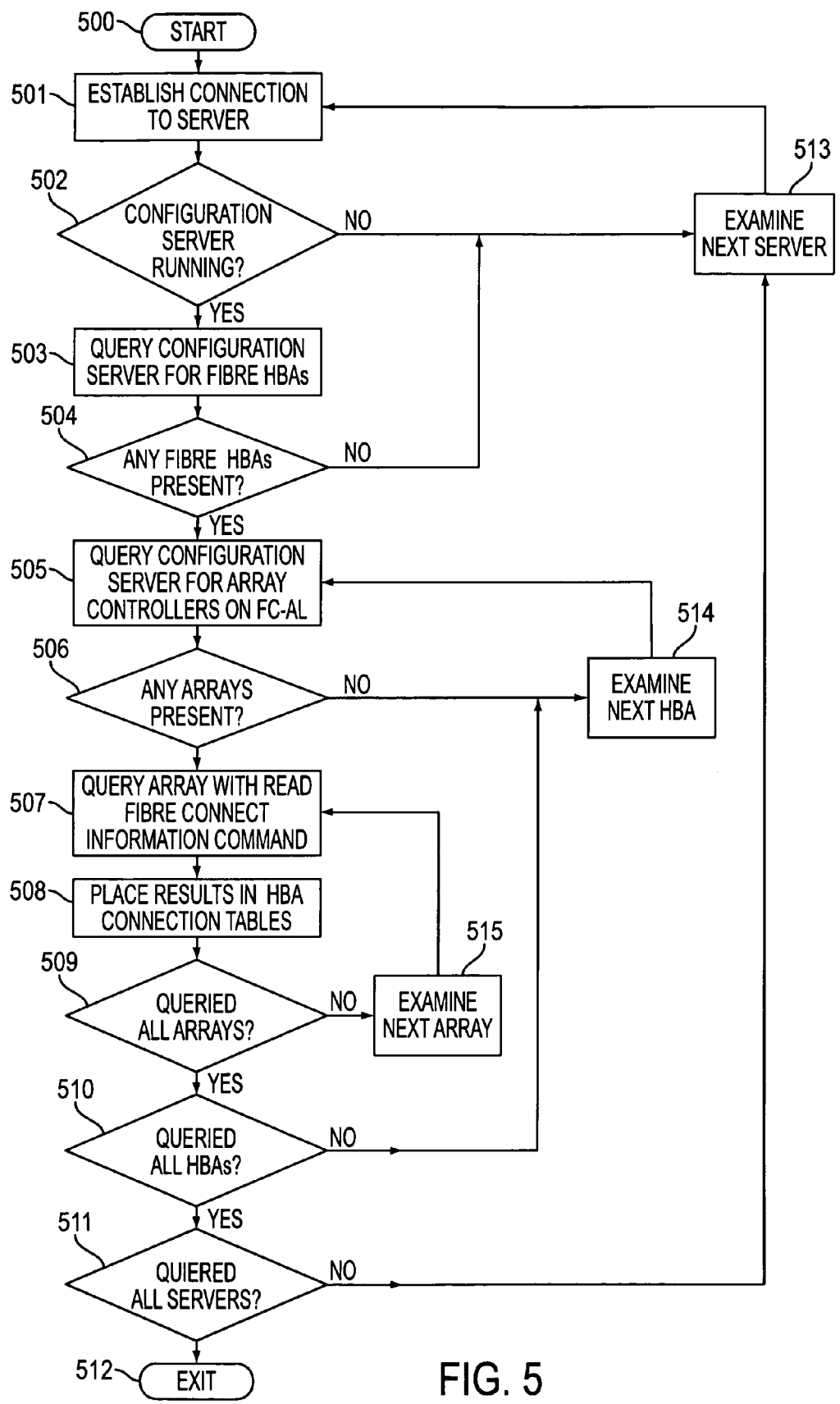
FIG. 5 is a diagrammatic illustration showing a flow-chart of an embodiment of the inventive storage network device mapping procedure.

We next describe a particular embodiment of the inventive mapping method having some optional features with respect to the diagrammatic flow chart illustration in FIG. 5. Referring to FIG. 3 and FIG. 5, the client configuration software 314 establishes communication (Step 501) with the server 302 through a network 301 or other connection, such as through a local area network (LAN) or wide area network (WAN), using Ethernet, internet, or other communication protocols that connect the server computer 302 to the client computer 300. Recall that the client computer 300 is the computer on which the configuration client software 314 is being executed. Also recall that the server computer 302 is the computer on which the configuration server software 313 is being executed. Note that the client computer 300 may establish communication with a server computer 302 that is not executing the configuration server software, but such server will be unable to query any attached RAID controllers. The mapping procedure then queries the server (Step 502) to determine if that server is executing the configuration server software. If not, the client software will perform no further queries to that particular server and will go on to examine the next server to be queried (Step 513) by repeating Step 501.

The server is then instructed by the configuration client software to query the configuration server for fibre channel HBAs (Step 503). If none are found, the client software will perform no further queries to that server, and will go on to examine the next server to be queried (Step 513).

The configuration server is then instructed by the configuration client software to query each fibre channel HBA present on the server for array controllers attached on the Fibre Channel Loop (Step 505). If no array controllers are present on that HBA, the configuration client software will make no further queries to that HBA and will go on to examine the remaining HBA on that server (Step 514).

At this point in the mapping procedure the configuration client software 314 instructs the configuration server software 313 to issue a Read Fibre Connection Information command to the array. The results of that command are returned by the configuration server software 313 to the configuration client software 314 through the LAN, WAN, or other connection 301, which place the returned results into the appropriate HBA connection table 403 (Step 508).

A determination is made as to whether all array controllers have been queried (Step 509) and, if not, the next array controller is queried (Step 515) by repeating Steps 507-509. Another determination is made as to whether all HBAs have been queried (Step 510) and, if not, the next HBA is examined (Step 514) in like manner. The procedure is similarly repeated until all servers have been queried (Step 511) and examined (Step 513), at which time the procedure ends (Step 512).

In the event that there are other storage devices 112-2 that may not understand or be capable of responding to the Read Fibre Information command, these storage devices can be recognized by the configuration server software 313 using the standard SCSI Inquiry command. This command allows the configuration server software 313 to determine that a storage device is attached to the fibre channel loop, but does not report the WWN of any of this type of device. As a result, the presence of a storage device attached to the loop can be reported back to the configuration client software 314 in the same way as other devices, that is, through the protocol being used on the communications channel such as the LAN/WAN 106, 108 connecting the client computer 104 to the server computer 110-2. Various protocols are known in the art and may be used in conjunction with the inventive structure, method, and computer program. The topology of these devices in the SAN can also be determined using the information about which server computer 110 the device is connected to. In this case, devices 112 connected to single server computer 110 systems can be determined, but devices connected to multiple server computers cannot be uniquely distinguished. In this event, the client server software assigns a special pseudo-WWN to each device and uses this pseudo-WWN in the appropriate HBA connection table 403. While these devices are part of the SAN, they are not capable of discriminating between different servers, so the WWN is not important. The pseudo-WWN may be, for example, a reserved or illegal WWN, such as for example ff.ff.ff.ff.ff.ff.ff.ff. or 00.00.00.00.00.00.00.00.

The configuration client application 314 or other client application program able to access the information returned then presents the topology and connectivity of the overall system or, where desired of portions thereof, and constructs and presents diagrams or tables to the operator based on the server table 400 and the associated HBA connection tables 403. These tables may be stored in the RAM of the client computer 300 for display purposes, or may be stored in the non-volatile storage of the client computer 300 for future reference. In one embodiment, the data in the tables is interpreted as a straightforward table or other data structure. The client server software displays the host name or IP address of each server 110, 302 along with a list of their attached HBAs 303, 305 and their associated WWNs 304, 306. Each of these in turn shows a list of the WWNs of the storage devices attached to each HBA. In other embodiments, the data is accessed by additional procedures which interpret and/or process the data and display this information in a graphical format.

Having described the structure of the Read Fibre Connection Information command and its operation in a storage system such as in a storage area network (SAN), we can now describe in greater detail an embodiment of a controller that may be used in conjunction with the inventive method and computer program product.

Figure 6:
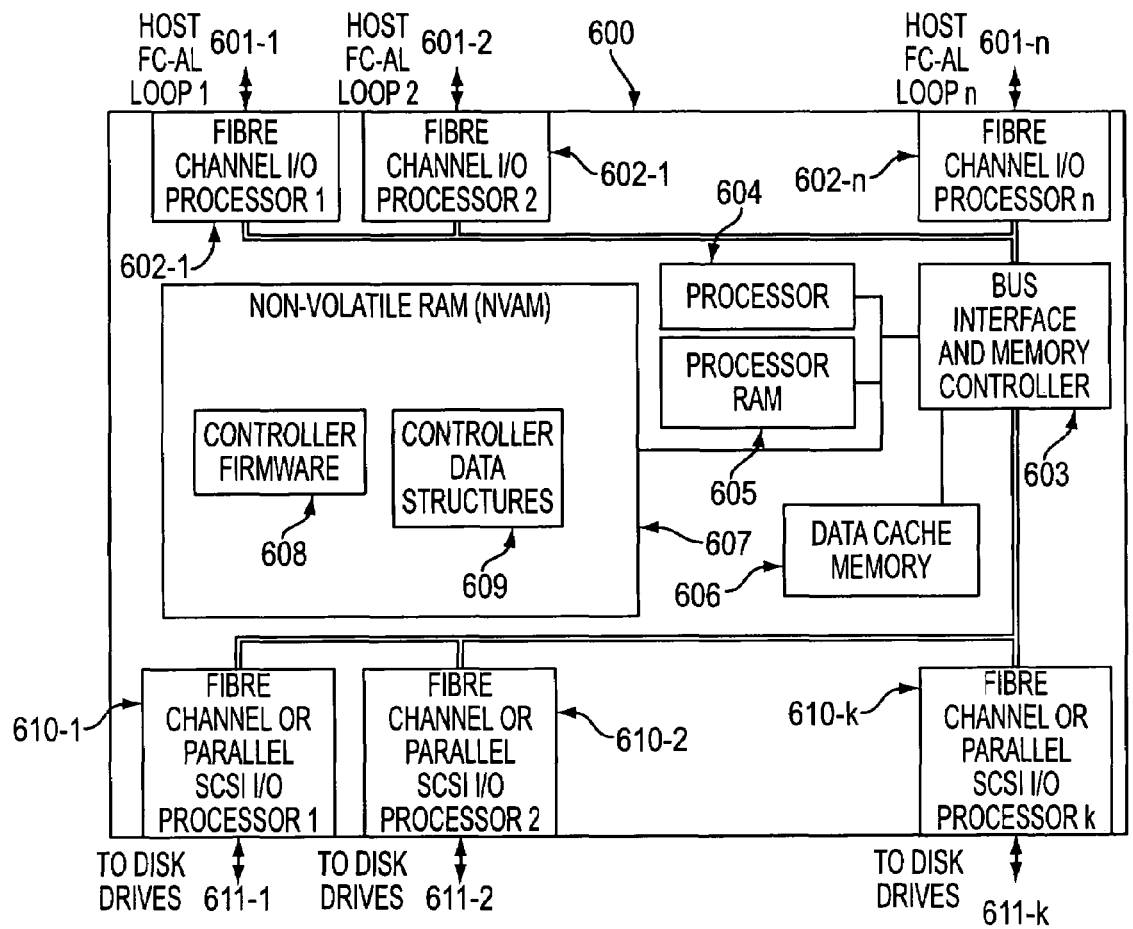
FIG. 6 is a diagrammatic illustration showing an embodiment of the controller hardware and firmware.

In one embodiment of the invention, the controller is a RAID controller such as illustrated in FIG. 6. The controller 600 is coupled to a server computer 110 through a Fibre-channel arbitrated loop (FC-AL) 601 via Fibre Channel I/O processors 602, and to the disk drives or other controlled devices by either a fibre channel arbitrated loop or by a parallel SCSI bus 611 (using for example the Fibre Channel I/O processors or the Parallel SCSI I/O processors). The controller 600 includes a processor 604 such as for example an Intel i960 microprocessor, random access memory (RAM) 605 coupled to the processor which stores the executable machine instructions (such as for example machine instructions implementing one or more of the inventive procedures during execution) and data structures or portions thereof (such as for example the inventive server table 400, and HBA connection tables 403), as well as non-volatile RAM (NVRAM) 607 for storing the controllers executable firmware 608 and permanent data structures 609. Permanent data structures may include configuration information, including the WWN(s) 310, 312 of the controller's Fibre Channel Ports 309, 311, and any other information required by the array controller in the event of a loss of power. Temporary data structures are stored in the controller's RAM 605 and are used to process data transfer requests (read and write) as the controller operates. These structures are temporary, and required only as long as the controller is working on a particular request. Information regarding the controller's WWN is stored in the controller permanent data structures 609, and may be optionally stored in a disk drive attached to the array. Bus interface and memory controller 603 controls activity from the processor, memories, and I/O processors on the buses in conventional manner.

Advantageously, the inventive method is implemented as a software or firmware computer program or programs. The client configuration software 314 is loaded into the client computer 300 and is executed by the client processor CPU. In an analogous manner, the server configuration software 313 is loaded into the server computer 302 and is executed by the server processor CPU. Storage and execution of each of the client and server configuration software are conventional and not described in detail here. The controller firmware 608 is loaded into the processor RAM 605 and then executed by the Processor 604.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims. All patents and publications referenced herein are hereby incorporated by reference.

I claim:

1. A method for generating a connection topology for a computer system of a type having at least one server, and at least one device controller coupled to said server through a host bus adapter, said method comprising:
   (a) querying said server to identify all host bus adapters to said server coupled;
   (b) querying each identified host bus adapter to identify all device controllers attached to each said identified host bus adapter;
   (c) issuing a SCSI read connection information command to each said identified device controller through the host bus adapter identifying the host bus adapter WWN to the device controller and requesting a response identifying the WWN for the device controller and for the host bus adapter to which the device controller is connected;
   (d) receiving, for each said identified device controllers, connection results identifying a first WWN of the device controller and a second WWN of the host bus adapter to which the device controller is connected;
   (e) storing the returned connection results in a data structure, the data structure comprising a server table having (i) a server entry for each server identified to the computer system that is connected to at least one device controller, each entry having a pointer to a particular host bus adapter connection table, the host bus adapter connection table capable of being different for each entry; and
   (f) generating a connection topology from the data structure identifying the topology of said computer system including the topology of the at least one server and all controllers that are coupled to said server.

2. The method in claim 1, wherein at least one of said device controller WWN identifies a storage away device controller coupled to said host bus adapter.

3. The method in claim 1, wherein:
   said data structure comprises a server identification table and at least one host bus adapter connection table associated with a particular host bus adapter; and
   each said server identification table stores at least one server WWN identifier, and each host bus adapter is linked to at least one server table by a pointer and stores at least one device controller WWN identifier.

4. The method in claim 1, wherein:
   said host bus adapters comprise SCSI-based fibre channel arbitrated loop bus adapters;
   said device controller is coupled for communication to said host bus adapters by a communication channel including a Fiber Channel arbitrated loop channel;
   said device controllers comprise RAID storage device away controllers;
   said data structure comprises a host bus adapter connection table;
   said computer system comprises a distributed computer system having a plurality of servers and a plurality of storage subsystems;
   said computer network includes a RAID storage area network (SAN); and
   said device comprise multiple storage subsystems connected to multiple server systems.

5. The method in claim 4, wherein said method further comprises the step of sending messages using a messaging protocol that permits a storage configuration tool to identify storage subsystems on said storage area network, and said messaging protocol is substantially independent of the operating system and channel type.

6. The method in claim 1, wherein:
   said host bus adapters comprise Fibre Channel arbitrated loop bus adapters, said read connection information command comprises a Read Fibre Connection Information command, and said Read Fibre Connection Information command returns a fibre channel port WWN of a device controller; and
   said Read Fibre Connection Information command returns a host bus adapter WWN of a fibre channel host bus adapter to which an array storage device is connected.

7. The method in claim 1, wherein said querying of said server is initiated by a request from an external client computer and said connection results are returned to said client computer, and said connection results identify all connections between a device controller and at least one server to said client.

8. The method in claim 7, wherein said server comprises an configuration server application software computer program executing on a server computer, and said client comprises a configuration client application software computer program executing on a computer selected from the group consisting of a client computer and said server computer.

9. The method in claim 8, wherein said server computer includes a plurality of host bus adapters and said disk array controller includes a plurality of Fibre Channel Ports, each of these host bus adapters and fibre channel ports being associated with a WWN.

10. The method in claim 8, wherein said configuration server application software computer program allows specific configuration and control commands to be sent by the server computer to the storage array controller from the configuration client.

11. The method in claim 8, wherein said storage array controller comprises a Fibre Channel compliant RAID controller.

12. The method in claim 8, wherein said configuration server application software computer program allows information from said device controller to be sent to the configuration client.

13. The method of claim 1, wherein the generating of a connection topology includes generating a graphical connection topology on a display device, the graphical display showing a complex connection of servers, device controllers, and storage systems to be mapped for the purpose of managing and configuring storage device controllers.

14. The method of claim 1, wherein said querying to identify all server host bus adapters is performed in response to a request by a client communicating with said server.

15. The method of claim 1, wherein:
   said read connection information command comprises a SCSI read connection information command; and
   said first WWN is to a particular port of the device controller when the device controller includes a plurality of device ports, and said second WWN is to a particular port of the host bus adapter when the host bus adapter includes a plurality of adapter ports.

16. The method of claim 1, wherein: the computer system includes a plurality of servers and the method further includes, prior to generating the topology, repeating each of the querying identified host adapter, issuing read connection information command, receiving connection results, and storing connection results steps for each server and generating a topology for the plurality of servers of the computer system including displaying devices and device controllers that are attached to single servers and to multiple servers.

17. The method of claim 1, the server table further having:
   (ii) an end of controller list entry in the host bus adapter connection tables containing a predetermined indicator to indicate the end of the list of device controllers attached to the host bus adapter; and
   (iii) a next host adapter entry in the host bus adapter connection tables including a pointer to the next host bus adapter connection table for that server where such next host bus adapter connection table exists or some other indicator to denote that there are no further host bus adapters attached to that server;
   the data structure further comprising the host bus adapter connection table containing the WWN of each host bus adapter connected to a server and the WWN of each device controller connected to the host bus adapter; and
   an instantiation of the host bus adapter connection table being stored on the or each of the servers in the computer system, and each instantiation of the host bus adapter connection table storing the WWN of the server host bus adapter in a first position of the host bus adapter connection table and a list of WWNs for each device controller attached to that host bus adapter in other positions of the host bus adapter connection table.

18. A computer program product for use in conjunction with a computer system of a type having at least one server, and at least one device controller coupled to said server through a host bus adapter, the computer program product comprising a computer readable storage medium and a computer program mechanism embedded therein, the computer program mechanism, comprising:
   (a) querying said server to identify all host bus adapters coupled to said server;
   (b) querying each host bus adapter to identify all device controllers attached to each said identified host bus adapter;
   (c) issuing a read connection information command to each said identified device controller through the host bus adapter identifying the host bus adapter WWN to the device controller and requesting a response identifying the WWN for the device controller and for the host bus adapter to which the device controller is connected;
   (d) receiving for each said identified device controllers, connection results identifying a first WWN of the device controller and a second WWN of the host bus adapter to which the device controller is connected;
   (e) storing the returned connection results in a data structure, the data structure comprising a server table having (i) a server entry for each server identified to the computer system that is connected to at least one device controller, each entry having a pointer to a particular host bus adapter connection table, the host bus adapter connection table capable of being different for each entry; and
   (f) generating a connection topology from the data structure identifying the topology of said computer system including the topology of the at least one server and all controllers that are coupled to said server.

19. A method for collecting connection information and generating a graphical system topology in a system of a type comprising at least one disk away controller coupled to at least one configuration server, the configuration server having a host bus adapter, the method comprising:
   generating a SCSI read fibre connection information command in the configuration server;
   issuing the SCSI read fibre connection information command to the at least one disk away controller through the host bus adapter;
   receiving a first WWN of the host bus adapter and a second WWN of the disk away controller responsive to the SCSI read fibre connection information command for each disk away controller and each host bus adapter;
   storing the received first and second WWN in a data structure, the data structure comprising a server table having (i) a server entry for each server identified to the computer system that is connected to at least one device controller, each entry having a pointer to a particular host bus adapter connection table, the host bus adapter connection table capable of being different for each entry; and
   generating a graphical connection topology diagram from the data stored in the data structure identifying the connection topology of said computer system including the topology of the at least one configuration server and all host bus adapters and away controllers having a WWN coupled to the configuration server.

* * * * *